(12) United States Patent
Inoue et al.

(10) Patent No.: US 7,572,833 B2
(45) Date of Patent: Aug. 11, 2009

(54) DRUG COMPOSITION COMPRISING DIPEPTIDYL ALDEHYDE DERIVATIVE

(75) Inventors: Jun Inoue, Kobe (JP); Masazumi Yamaguchi, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 1010 days.

(21) Appl. No.: 10/415,295

(22) PCT Filed: Sep. 27, 2001

(86) PCT No.: PCT/JP01/08514

§ 371 (c)(1),
(2), (4) Date: Apr. 28, 2003

(87) PCT Pub. No.: WO02/34252

PCT Pub. Date: May 2, 2002

(65) Prior Publication Data

US 2004/0048929 A1    Mar. 11, 2004

(30) Foreign Application Priority Data

Oct. 26, 2000   (JP) .............................. 2000-327677

(51) Int. Cl.
*A61K 31/18*   (2006.01)
(52) U.S. Cl. ..................... 514/601; 514/605
(58) Field of Classification Search ............ 514/19, 514/605
See application file for complete search history.

(56) References Cited

U.S. PATENT DOCUMENTS

| 5,506,243 A | 4/1996 | Ando et al. | |
|---|---|---|---|
| 5,624,898 A * | 4/1997 | Frey, II | 514/12 |
| 5,753,296 A * | 5/1998 | Girsh | 426/593 |
| 5,945,121 A | 8/1999 | Kato et al. | |
| 6,057,290 A * | 5/2000 | Fukiage et al. | 514/12 |
| 6,214,800 B1 * | 4/2001 | Fukiage et al. | 514/19 |
| 6,342,531 B1 * | 1/2002 | Azuma et al. | 514/601 |
| 6,423,691 B1 * | 7/2002 | Azuma et al. | 514/19 |
| 6,551,999 B1 * | 4/2003 | Fukiage et al. | 514/19 |

FOREIGN PATENT DOCUMENTS

| EP | 0 622 072 | 11/1994 |
|---|---|---|
| EP | 622 072 | 11/1994 |
| EP | 1 123 919 | 8/2001 |
| EP | 1 221 315 | 7/2002 |
| JP | 58-38219 | 3/1983 |
| JP | 6-329533 | 11/1994 |
| JP | 11-199488 | 7/1999 |
| JP | 2000093093 | * 4/2000 |
| JP | 2000290170 | * 10/2000 |
| WO | 90/11780 | 10/1990 |
| WO | 96/19211 | 6/1996 |
| WO | WO 97/21690 | 6/1997 |
| WO | 99/44624 | 9/1999 |
| WO | 99/48522 | 9/1999 |
| WO | 01/26648 | 4/2001 |
| WO | 01/41757 | 6/2001 |

OTHER PUBLICATIONS

M. Yokota et al., "Calpain Inhibitor Entrapped in Liposome Rescues Ischemic Neuronal Damage", Brain Research, Feb. 1999, vol. 819, pp. 8-14.

C. Fukiage et al., "SJA6017, A Newly Synthesized Peptide Aldehyde Inhibitor of Calpain: Amelioration of Cataract in Cultured Rat Lenses", Biochimica et Biophysica Acta, 1997, vol. 1361, pp. 304-312.

Database WPI Week 200148, Derwent Publications Ltd., London, GB; AN 2001-451587, XP002436813 & WO 01/41757 A1 (Senju Pharm Co Ltd) Jun. 14, 2001 *abstract*.

* cited by examiner

*Primary Examiner*—Alton N Pryor
(74) *Attorney, Agent, or Firm*—Wenderoth, Lind & Ponack, LLP.

(57) ABSTRACT

The present invention provides a preparation containing a compound of the formula (I)

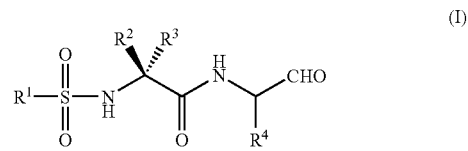

wherein $R^1$ is an alkyl group having 1 to 4 carbon atoms or an optionally substituted aryl group having 6 to 10 carbon atoms; $R^2$ and $R^3$ are the same or different and each is hydrogen or an alkyl group having 1 to 4 carbon atoms, or $R^2$ and $R^3$ in combination form a ring having 3 to 7 carbon atoms; and $R^4$ is a lower alkyl group optionally substituted by aryl, cycloalkyl or aromatic heterocyclic residue, or a pharmaceutically acceptable salt thereof together with a lipid. The preparation shows improved stability and improved absorption and penetration into tissue.

11 Claims, 3 Drawing Sheets

DRUG COMPOSITION COMPRISING DIPEPTIDYL ALDEHYDE DERIVATIVE

This application is a U.S. national stage of International Application No. PCT/JPO1/08514 filed Sept. 27, 2001.

1. Technical Field

The present invention relates to a pharmaceutical composition comprising a dipeptidyl aldehyde derivative and a lipid. In addition, the present invention relates to a method for improving the stability of a dipeptidyl aldehyde derivative and a method for promoting absorption or improving penetration into tissue.

1. Background Art

A compound of the formula (I)

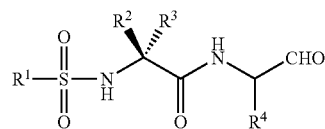

wherein $R^1$ is an alkyl group having 1 to 4 carbon atoms or an optionally substituted aryl group having 6 to 10 carbon atoms; $R^2$ and $R^3$ are the same or different and each is a hydrogen or an alkyl group having 1 to 4 carbon atoms, or $R^2$ and $R^3$ in combination form a ring having 3 to 7 carbon atoms; and $R^4$ is a lower alkyl group optionally substituted by aryl, cycloalkyl or aromatic heterocyclic residue [hereinafter sometimes to be referred to as dipeptidyl aldehyde derivative (I)] and a pharmaceutically acceptable salt thereof are disclosed in JP-A-10-147564 (U.S. Pat. No. 6,214,800). This compound has an inhibitory activity on cysteine protease such as calpain and the like, and is known to be useful as a pharmaceutical preparation for the prophylaxis or treatment of cysteine protease-associated diseases, such as ischemic diseases, immune diseases, Alzheimer's disease, osteoporosis, diseases caused by brain tissue impairment (e.g., cerebral vasospasm, cerebral thrombosis, cerebral infarction, cerebral embolism, intracerebral hemorrhage, subarachnoid hemorrhage, hypertensive encephalopathy, transient cerebral ischemic attack, multiinfarct dementia, cerebral arteriosclerosis, Huntington's disease and the like), cataract, glaucoma (e.g., open angle glaucoma, low tension glaucoma, closed angle glaucoma and the like), retinochoroidal disorders (e.g., retinal vascular abnormalities such as occlusion of retinal vessels, retinal periphlebitis, Eales' disease, ischemic ophthalmic syndrome, retinal arteriolar macroaneurysm and the like, retinopathy due to hypertension or renal disease, diabetic retinopathy, retinal pigment epitheliopathy, retinal dystrophy, macular dystrophy, retinochoroidal atrophy, chorioretinopathy, macular degeneration, macular edema, detachment of the retinal pigment epithelium, detachment of the retina, degenerative retinoschisis, retinoblastoma, retinal pigment epithelium tumor, optic disc capirally angioma and the like), eyeball posterior complications due to photocoagulation (e.g., macular edema, detachment of the retina, optic neuritis, visual field abnormalities, disturbance of light sense, color vision deficiency and the like) and the like, or as an agent for the prophylaxis or treatment of angiogenesis, detachment of the retina and the like [JP-A-10-147566 (U.S. Pat. No. 6,214,800), WO99/48522, WO99/.44624].

However, dipeptidyl aldehyde derivative (I) is hardly soluble in water and when dissolved using a solubilizer, it becomes unstable. When used for oral administration or topical administration, moreover, absorption and penetration into tissue of this derivative after administration are not satisfactory. For sufficient exhibition of efficacy, therefore, the dose needs to be increased.

As a pharmaceutical preparation containing a lipid, liposome is known. Liposome can be used for the targeting of a drug, because it is superior in compatibility with living organisms, permits easy control of surface properties, size and the like, permits enclosure of various compounds having diverse properties, and the like [D. D. Lasic, "Liposomes: from basic to applications", Elsevier Science Publishers, pp. 261-471 (1993)]. In practice, however, liposome is associated with problems in that the inclusion rate of drug into liposome is impractically low and the like, due to which it has so far produced few examples of clinical success, such as a liposome preparation of doxorubicin and the like [D. D. Lasic, Nature 380, 561-562 (1996)].

DISCLOSURE OF THE INVENTION

The invention aims at creation of a pharmaceutical composition of dipeptidyl aldehyde derivative (I) that shows fine absorption by oral administration, and a pharmaceutical composition that enhances penetration thereof into tissue by topical administration. Further, it aims at creation of a pharmaceutical composition of dipeptidyl aldehyde derivative (I), which is stable over a long period of time even in water and which can be administered by injection or instillation into the eye.

Accordingly, the present invention relates to (1) a pharmaceutical composition containing a compound represented by the formula (I)

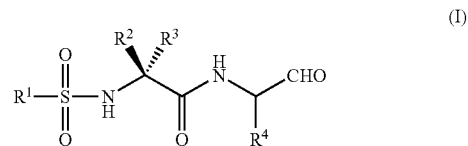

wherein
$R^1$ is an alkyl group having 1 to 4 carbon atoms or an optionally substituted aryl group having 6 to 10 carbon atoms;
$R^2$ and $R^3$
are the same or different and each is hydrogen or an alkyl group having 1 to 4 carbon atoms, or $R^2$ and $R^3$ in combination form a ring having 3 to 7 carbon atoms; and
$R^4$ is a lower alkyl group optionally substituted by aryl, cycloalkyl or aromatic heterocyclic residue,
or a pharmaceutically acceptable salt thereof and a lipid, (2) the pharmaceutical composition of the above-mentioned (1), wherein $R^1$ in the formula (I) is phenyl or naphthyl, which is optionally substituted by fluorine, chlorine or methyl, (3) the pharmaceutical composition of the above-mentioned (1), wherein $R^1$ in the formula (I) is a group selected from methyl, 4-fluorophenyl, 4-chlorophenyl, p-tolyl and 2-naphthyl, (4) the pharmaceutical composition of the above-mentioned (1), wherein, in the formula (I), $R^2$ is propyl, isopropyl or tert-butyl, and $R^3$ is hydrogen, (5) the pharmaceutical composition of the above-mentioned (1), wherein, in the formula (I), $R^2$ is isopropyl and $R^3$ is hydrogen, (6) the pharmaceutical composition of the above-mentioned (1), wherein, in the formula (I), $R^2$ and $R^3$ in combination form cyclopentylidene or cyclohexylidene, (7) the pharmaceutical composition of the above-mentioned (1) wherein, in the formula (I), $R^4$ is a group selected from isobutyl, benzyl, cyclohexylmethyl and indol-3-yl-methyl, (8) the pharmaceutical composition of the above-mentioned (1), wherein the compound of the formula (I) is N-(4-fluorophenylsulfonyl)-L-valyl-L-leucinal or a pharmaceutically acceptable salt thereof, (9) the pharmaceutical composition of any of the above-mentioned (1)-(8), wherein a lower limit of the amount of the lipid constituting the pharmaceutical composition is about 5 parts by weight and an upper limit thereof is about 14 parts by weight, per 1 part by weight of the compound of the formula (I) or a pharmaceutically acceptable salt thereof,

(10) the pharmaceutical composition of the above-mentioned (9), wherein the compound of the formula (I) or a pharmaceutically acceptable salt thereof and a lipid form a complex,

(11) the pharmaceutical composition of the above-mentioned (10), wherein the complex is a liposome,

(12) the pharmaceutical composition of the above-mentioned (11), wherein the amount of the lipid constituting the liposome is about 7-about 14 parts by weight, per 1 part by weight of the compound of the formula (I) or a pharmaceutically acceptable salt thereof,

(13) the pharmaceutical composition of any of the above-mentioned (1)-(12), which is used for the prophylaxis or treatment of ischemic disease, immune disease, Alzheimer's disease, osteoporosis, diseases due to brain tissue impairment, cataract, glaucoma, retinochoroidal disorder, eyeball posterior complication due to photocoagulation, diseases accompanying angiogenesis and the like,

(14) the pharmaceutical composition of any of the above-mentioned (1)-(13), which is for an oral administration,

(15) the pharmaceutical composition of any of the above-mentioned (1)-(13), which is for eye drops,

(16) the pharmaceutical composition of any of the above-mentioned (1)-(13), which is for an injection,

(17) a method for improving the stability of a compound represented by the formula (I), which comprises bringing a compound represented by the formula (I) or a pharmaceutically acceptable salt thereof into contact with a lipid,

(18) a method for promoting the absorption of the compound represented by the formula (I), which comprises bringing the compound represented by the formula (I) or a pharmaceutically acceptable salt thereof into contact with a lipid, and

(19) a method for improving penetration of the compound represented by the formula (I) into a tissue, which comprises bringing the compound represented by the formula (I) or a pharmaceutically acceptable salt thereof into contact with a lipid.

In the above-mentioned formula (I), the alkyl group having 1 to 4 carbon atoms mentioned for $R^1$ includes methyl, ethyl, propyl, isopropyl, butyl, isobutyl, sec-butyl, tert-butyl and the like. Of these, methyl is preferred. The aryl group having 6 to 10 carbon atoms for $R^1$ includes phenyl, naphthyl, indenyl, azulenyl and the like. Preferred are phenyl and naphthyl. The substituent group which may be present on the aryl group includes, for example, halogen atom (e.g., fluorine, chlorine and the like), alkyl having 1 to 5 carbon atoms, trifluoromethyl, alkoxy having 1 to 5 carbon atoms, hydroxy, acyloxy having 2 to 5 carbon atoms, carboxyl and acyl group having 2 to 5 carbon atoms. Preferred are halogen atom and alkyl group having 1 to 5 carbon atoms. The more preferred are fluorine, chlorine and methyl. Preferred examples of the optionally substituted aryl group having 6 to 10 carbon atoms for $R^1$ are 4-fluorophenyl, 4-chlorophenyl, p-tolyl and 2-naphthyl.

The alkyl group having 1 to 4 carbon atoms mentioned for $R^2$ and $R^3$ includes methyl, ethyl, propyl, isopropyl, butyl, isobutyl, sec-butyl, tert-butyl and the like. Preferred are propyl, isopropyl and tert-butyl. The more preferred is isopropyl. Referring to $R^2$ and $R^3$, one of $R^2$ and $R^3$ is preferably hydrogen and the other is propyl, isopropyl, isobutyl or tert-butyl. More preferably, $R^2$ is propyl, isopropyl, isobutyl or tert-butyl and $R^3$ is hydrogen. Still more preferably, $R^2$ is isopropyl and $R^3$ is hydrogen.

The ring having 3 to 7 carbon atoms which may be formed by $R^2$ and $R^3$ in combination includes cyclopropylidene, cyclobutylidene, cyclopentylidene, cyclohexylidene, cycloheptylidene and the like. Cyclopentylidene and cyclohexylidene are particularly preferred.

The lower alkyl group mentioned for $R^4$ includes linear or branched alkyl group having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, 4-methylpentyl, 1,1-dimethylbutyl, 2,2-dimethylbutyl, 3,3-dimethylbutyl, 2-ethylbutyl and the like. Preferred are methyl and isobutyl. Examples of aryl group that optionally substitutes the lower alkyl group for $R^4$ include phenyl, 1-naphthyl, 2-naphthyl and the like. Of these, phenyl is preferable. Examples of cycloalkyl group that optionally substitutes the lower alkyl group for $R^4$ include cyclopropyl, cyclobutyl, cyclopentyl, cyclohexyl and the like. Of these, cyclohexyl is preferable. Examples of aromatic heterocyclic residue that optionally substitutes the lower alkyl group for $R^4$ include monocyclic heterocyclic residue and fused heterocyclic residue substituted by oxygen, nitrogen and sulfur atom. Examples of monocyclic heterocyclic residue include pyrrolyl, furanyl, thiophenyl, oxazolyl, thiazolyl, imidazolyl, pyrazolyl, pyridyl and the like and examples of fused heterocyclic residue include indolyl, quinolyl, benzothiophenyl, benzofuranyl, indazolyl, quinazolinyl, phthalazinyl, quinoxalinyl and the like. Of these, indolyl is preferable. Preferred examples of the lower alkyl group optionally substituted by aryl, cycloalkyl or aromatic heterocyclic residue as expressed by $R^4$ are isobutyl, benzyl, cyclohexylmethyl and indol-3-ylmethyl.

The salt of the compound represented by the formula (I) in the present invention is preferably a physiologically acceptable salt, which is exemplified by a salt with an inorganic base, a salt with an organic base, a salt with an inorganic acid, a salt with an organic acid, a salt with a basic or an acidic amino acid and the like. Preferable examples of the salt with inorganic base include alkali metal salts such as sodium salt, potassium salt and the like; alkaline earth metal salts such as calcium salt, magnesium salt and the like; aluminum salt, ammonium salt and the like. Preferable examples of the salt with organic base include salts with trimethylamine, pyridine, picoline, ethanolamine, diethanolamine, triethanolamine, dicyclohexylamine, N,N-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like, and preferable examples of the salt with acidic amino acid include salts with aspartic acid, glutamic acid and the like.

Specific examples of dipeptidyl aldehyde derivative (I) include N-(2-naphthalenesulfonyl)-L-valyl-L-leucinal, N-(4-fluorophenylsulfonyl)-L-valyl-L-leucinal, N-(4-chlorophenylsulfonyl)-L-valyl-L-leucinal, N-(4-methylphenylsulfonyl)-L-valyl-L-leucinal, N-(2-naphthalenesulfonyl)-L-tert-leucyl-L-leucinal, N-(4-fluorophenylsulfonyl)-D-valyl-L-leucinal, N-(4-fluorophenylsulfonyl)-L-norleucyl-L-leucinal, N-(4-fluorophenylsulfonyl)-L-norvalyl-L-leucinal, 1-(2-naphthalenesulfonylamino)cyclopentanecarbonyl-L-leucinal, N-(2-naphthalenesulfonyl)-L-tert-leucyl-L-phenylalaninal, N-(4-fluorophenylsulfonyl)-L-valyl-L-phenylalaninal, N-(2-naphthalenesulfonyl)-L-valyl-L-phenylalaninal, N-(4-chlorophenylsulfonyl)-L-valyl-L-phenylalaninal, N-(4-methylphenylsulfonyl)-L-valyl-L-phenylalaninal, N-(2-naphthalenesulfonylamino)cyclohexanecarbonyl-L-phenylalaninal, 1-(2-naphthalenesulfonylamino)cyclopentanecarbonyl-L-phenylalaninal, N-(4-chlorophenylsulfonyl)-L-valyl-L-tryptophanal, N-(4-fluorophenylsulfonyl)-L-valyl-L-tryptophanal, 1-(2-naphthalenesulfonylamino)-cyclohexanecarbonyl-L-tryptophanal, N-(2-naphthalenesulfonyl)-L-tert-leucyl-L-tryptophanal, N-(4-fluorophenylsulfonyl)-L-valyl-L-cyclohexylalaninal, N-(2-naphthalenesulfonyl)-L-valyl-L-cyclohexylalaninal, N-(4-chlorophenylsulfonyl)-L-valyl-L-cyclohexylalaninal, N-(4-fluorophenylsulfonyl)-D-valyl-L-leucinal, N-(4-fluorophenylsulfonyl)-L-valyl-D-leucinal, N-(4-fluorophenylsulfonyl)-L-valyl-L-alaninal and N-methylsulfonyl-L-valyl-L-leucinal and the like, which are produced according to JP-A-10-147564 (U.S. Pat. No. 6,214,800).

The lipid usable in the present invention includes a compound selected from the group consisting of glycerophospholipid (phosphatidylcholine, phosphatidylglycerol, phosphatidylinositol, phosphatidylserine, phosphatidylethanolamine, N-monomethoxypolyethylene glycol succinyl phosphatidylethanolamine and the like), glyceroglycolipid (digalactosyldiglyceride, galactosyldiglyceride and the like), sphingophospholipid (sphingomyelin and the like), sphingoglycolipid (cerebroside, ganglioside and the like), sterols (cholesterol, cholesterol hemisuccinate, 3β-[N-(N', N'-dimethylaminoethane)-carbamoyl]-cholesterol, ergosterol, lanosterol and the like), synthetic organic compounds having alkyl, alkenyl, alkanoyl or alkenoyl chain having 10-20 carbon atoms (stearic acid, stearylamine, stearic acid hydrazide, stearic acid ester, N-[1-(2,3-dioleoyloxy)propyl]-N,N,N-trimethylammonium chloride, N-α-trimethylammonioacetyldodecyl-D-glutamate chloride, O-palmitoylpullulan and the like) and the like.

The above-mentioned lipids (phosphatidylcholine, phosphatidylglycerol, phosphatidylinositol, phosphatidylserine, phosphatidylethanolamine, digalactosyldiglyceride, galactosyldiglyceride, sphingomyelin, cerebroside, ganglioside, N-monomethoxypolyethylene glycol succinyl phosphatidylethanolamine and the like) each have two saturated or unsaturated fatty acid ester chains, and a lipid wherein the fatty acid (alkanoyl or alkenoyl group) moiety has 10-18 carbon atoms can be used as a constituent component in the present invention. As the "alkanoyl or alkenoyl group having 10-18 carbon atoms", decylyl, undecylyl, lauroyl, tridecylyl, myristoyl, pentadecylyl, palmitoyl, heptadecylyl, stearoyl, oleoyl group and the like can be used. Of these, preferred are lauroyl, myristoyl, palmitoyl and stearoyl group.

As the above-mentioned lipid, those generally sold as a reagent and the like can be obtained and used.

In addition, when a mixture containing a lipid generally having fatty acid ester chain having various carbon atoms and/or unsaturation degrees can be obtained, such as egg yolk lecithin, soybean lecithin and the like, it can be used as it is without separation or purification into single components.

Moreover, the above-mentioned lipid and egg yolk lecithin, as well as soybean lecithin and the like may be used alone or in a suitable combination of two or more kinds thereof.

In the present invention, a lipid having a water-soluble polymer chain can be also used. Examples of such water-soluble polymer chain include polyethylene glycol (PEG), polyacrylamide, polysaccharides such as pullulan, and the like. As a lipid having a water-soluble polymer chain, for example, N-monomethoxypolyethylene glycol succinyl phosphatidylethanolamine, O-($C_{10-18}$ alkanoyl or alkenoyl) pullulan, N-($C_{10-18}$ alkanoyl or alkenoyl)polyacrylamide and the like can be used. Preferably, it is N-monomethoxypolyethylene glycol succinyl di($C_{10-18}$ alkanoyl or alkenoyl)phosphatidylethanolamine, wherein the PEG moiety has an average molecular weight of 1000-5000, or O-palmitoylpullulan, most preferably, N-monomethoxypolyethylene glycol succinyl distearoyl phosphatidylethanolamine, wherein the PEG moiety has an average molecular weight of 2000.

Using a lipid having such water-soluble polymer, a pharmaceutical composition superior in residence in blood and accumulation property in the objective tissue can be produced.

Where necessary, an additive such as α-tocopherol and the like, can be used as a lipid constituting component aiming at an antioxidizing action and the like.

The pharmaceutical composition of the present invention means a state where dipeptidyl aldehyde derivative (I) or a pharmaceutically acceptable salt thereof, and a lipid form a mixture or a complex.

The above-mentioned "mixture" may be homogeneous or heterogeneous and refers to the state where dipeptidyl aldehyde derivative (I) or a pharmaceutically acceptable salt thereof, and a lipid are admixed, which, upon dispersion in water, permits easy separation of dipeptidyl aldehyde derivative (I) or a pharmaceutically acceptable salt thereof from the lipid.

To give a mixture, dipeptidyl aldehyde derivative (I) or a pharmaceutically acceptable salt thereof and a lipid are each processed into fine particles, which are, for example, triturated in a mortar, mechanically mixed in a stirrer, or thoroughly shaken in a plastic bag and the like.

The above-mentioned "complex" means a state where a bilayer membrane lipid assembly and dipeptidyl aldehyde derivative (I) or a pharmaceutically acceptable salt thereof are aggregated (assembly of molecules, ions, atoms and the like) by the interaction between molecules such as a cohesive force (e.g., van der Waals force, hydrogen bond, electrostatic interaction and the like), and encompasses a state where dipeptidyl aldehyde derivative (I) or a pharmaceutically acceptable salt thereof is simply bonded to the surface of a bilayer membrane of a lipid, a state where dipeptidyl aldehyde derivative (I) or a pharmaceutically acceptable salt thereof has partially entered a lipid bilayer membrane, and a state where dipeptidyl aldehyde derivative (I) or a pharmaceutically acceptable salt thereof is completely incorporated into a lipid bilayer membrane. The complex is a concept that includes "liposome". The "liposome" means a closed vesicle consisting of a bilayer membrane lipid assembly and an internal aqueous phase, wherein dipeptidyl aldehyde derivative (I) or a pharmaceutically acceptable salt thereof generally forms the above-mentioned complex with a membrane lipid assembly that constitutes the liposome, or may be enclosed in the aqueous phase in the liposome. As the aqueous phase constituting the inside of a liposome, an aqueous sodium chloride solution, a buffer (phosphate buffer, acetate buffer, sodium dihydrogenphosphate, disodium hydrogenphosphate and the like), an aqueous solution of monosaccharides or disaccharides (aqueous solution of glucose, aqueous solution of trehalose and the like), and the like can be generally used.

The complex can be prepared by dissolving dipeptidyl aldehyde derivative (I) or a pharmaceutically acceptable salt thereof and a lipid in a suitable solvent to give a homogeneous solution, and removing the solvent. For example, dipeptidyl aldehyde derivative (I) and lecithin are dissolved in an organic solvent such as ether, chloroform, methanol, ethanol and the like to give a homogeneous solution, from which the solvent is removed and the residue is sufficiently dried.

The liposome can be obtained by a general production method of liposomes. For example, phospholipid or glycolipid and the like and dipeptidyl aldehyde derivative (I) are homogenized and a liposome is prepared to encapsulate dipeptidyl aldehyde derivative (I) in the liposome, or a liposome is prepared in advance from phospholipid, glycolipid and the like and dipeptidyl aldehyde derivative (I) may be encapsulated. As the preparation method of liposome, known methods such as thin membrane method, surfactant removal method, ultrasonication method, ether infusion method, high pressure injection emulsification method, extrusion method and the like are exemplified. According to the thin membrane method, for example, phospholipid is dissolved in an organic solvent such as ether, chloroform and the like and placed in a glass container such as a round-bottom flask and the like. The organic solvent is removed by an evaporator or under a nitrogen stream to form a lipid thin membrane on a glass surface. By adding an aqueous solution thereto and applying a mechanical vibration, a liposome suspension can be obtained. For encapsulation of dipeptidyl aldehyde derivative (I) in a liposome prepared in advance, dipeptidyl aldehyde derivative (I) in a solid state and a liposome suspension are mixed and the mixture is applied to freeze-thawing or ultrasonication.

The amount of the lipid to be added to the pharmaceutical composition of the present invention is about 5 parts by weight, preferably about 6 parts by weight, more preferably about 7 parts by weight, for a lower limit, and about 14 parts by weight, preferably about 13 parts by weight, more preferably about 12 parts by weight, for an upper limit, per 1 part by weight of dipeptidyl aldehyde derivative (I) or a pharmaceutically acceptable salt thereof. When the amount of the lipid to be added is smaller than about 5 parts by weight, absorption property and penetration into tissue of dipeptidyl aldehyde derivative (I) or a pharmaceutically acceptable salt thereof are not improved beyond a certain level, and when it is not less than about 14 parts by weight, the dose needs to be increased to ensure sufficient efficacy. When a liposome is prepared and the amount of the lipid to be added is not less than about 7 parts by weight, dipeptidyl aldehyde derivative (I) or a pharmaceutically acceptable salt thereof is encapsulated well in a liposome. When the amount of the lipid to be added is less than about 7 parts by weight, only a part of the dipeptidyl aldehyde derivative (I) or a pharmaceutically acceptable salt thereof can be encapsulated in a liposome. Therefore, the amount of the lipid to be added to the liposome is preferably about 7-about 14 parts by weight, more preferably about 10-about 12 parts by weight, per 1 part by weight of dipeptidyl aldehyde derivative (I) or a pharmaceutically acceptable salt thereof.

The pharmaceutical composition of the present invention is administered systemically or topically to a warm-blooded animal (e.g., human, rat, mouse, rabbit, bovine, swine, dog, cat and the like).

When the pharmaceutical composition of the present invention is to be produced as a liquid for oral administration, eye drops or injection, it can be prepared by dispersing a mixture or a complex, preferably a complex, in a solution containing, as appropriate, a pharmaceutically acceptable additive such as an isotonicity agent (sodium chloride, potassium chloride, glycerin, mannitol, sorbitol, boric acid, glucose, propylene glycol and the like), a buffer (phosphate buffer, acetate buffer, borate buffer, carbonate buffer, citrate buffer, Tris buffer, glutamic acid, epsilon aminocaproic acid and the like), a preservative (p-oxybenzoates, benzalkonium chloride, chlorobutanol, benzyl alcohol, sodium dehydroacetate, sodium edetate, boric acid and the like), a thickener (hydroxyethylcellulose, hydroxypropylcellulose, polyvinyl alcohol, polyethylene glycol and the like), a stabilizer (sodium hydrogensulfite, sodium thiosulfate, sodium edetate, sodium citrate, ascorbic acid, dibutylhydroxytoluene and the like), a pH adjusting agent (hydrochloric acid, sodium hydroxide, phosphoric acid, acetic acid and the like) and the like.

When the pharmaceutical composition of the present invention is to be produced particularly as a liposome preparation for oral administration, eye drops or injection, it can be prepared by adding a pharmaceutically acceptable additive, such as an isotonicity agent (sodium chloride, potassium chloride, glycerin, mannitol, sorbitol, boric acid, glucose, propylene glycol and the like), a buffer (phosphate buffer, acetate buffer, borate buffer, carbonate buffer, citrate buffer, Tris buffer, glutamic acid, epsilon aminocaproic acid and the like), a preservative (p-oxybenzoates, benzalkonium chloride, chlorobutanol, benzyl alcohol, sodium dehydroacetate, sodium edetate, boric acid and the like), a thickener (hydroxyethylcellulose, hydroxypropylcellulose, polyvinyl alcohol, polyethylene glycol and the like), a stabilizer (sodium hydrogensulfite, sodium thiosulfate, sodium edetate, sodium citrate, ascorbic acid, dibutylhydroxytoluene and the like), pH adjusting agent (hydrochloric acid, sodium hydroxide, phosphoric acid, acetic acid and the like) and the like, to a prepared liposome suspension.

While the amount of the additive to be used for preparing the pharmaceutical composition of the present invention into a liquid for oral administration, eye drops or injection, or a liposome preparation for oral administration, eye drops or injection varies depending on the kind of the additive to be used, use and the like, it may be an amount corresponding to a concentration capable of achieving the object of the additive. An isotonicity agent is generally added in a concentration of about 0.5-about 5.0 w/v %, to make the osmotic pressure about 229-about 343 mOsm. A buffer is added in a concentration of about 0.01-about 2.0 w/v %, a thickener is added in a concentration of about 0.01-about 1.0 w/v %, a stabilizer is added in a concentration of about 0.001-about 1.0 w/v %. A pH adjusting agent is added as appropriate and adjusted to generally about 3-about 9, preferably about 4-about 8.

The pharmaceutical composition of the present invention can be prepared into a solid preparation, such as powder, granule, tablet and capsule and the like. For preparation into granule or tablet, a suitable additive (lactose, sucrose, glucose, starch, crystalline cellulose and the like), a sugar alcohol (mannitol, sorbitol and the like), a binder (starch paste solution, hydroxypropylcellulose solution, carmellose solution, gum arabic solution, gelatin solution, sodium alginate solution and the like), a disintegrant (starch, carmellose sodium, calcium carbonate and the like), a lubricant (magnesium stearate, talc, stearic acid, calcium stearate and the like) and the like is admixed as appropriate with a mixture or a complex, and according to, for example, general rules for preparations in The Japanese Pharmacopoeia, 14th Ed., the mixture is prepared into granule or tablet. The granule and tablet may contain a coloring agent, an aromatic substance, a flavoring agent and the like as necessary. These granule and tablet may be coated with a suitable coating agent (gelatin, sucrose, gum arabic, carnauba wax and the like), enteric coating agent (e.g., cellulose acetate phthalate, methacrylic acid copolymer, hydroxypropylcellulose phthalate, carboxymethylethylcellulose and the like) and the like. When a capsule is to be prepared, a mixture or a complex may be filled as it is, or a suitable excipient, such as magnesium stearate, calcium stearate, talc, light silicic anhydride and the like for improving fluidity and lubrication, crystalline cellulose, lactose and the like for compression fluidity, the above-mentioned disintegrant and the like may be added to a mixture or a complex, and the mixture is uniformly mixed or granulated, or such granule may be coated with a suitable coating agent and filled, or a suitable excipient and the like are added to a mixture or a complex and the mixture is encapsulated in a capsule base having increased plasticity by adding glycerin, sorbitol and the like to a suitable capsule base (gelatin and the like). Such capsule agents may contain, where necessary, a coloring agent, a preservative [sulfur dioxide, p-oxybenzoates (methyl p-oxybenzoate, ethyl p-oxybenzoate, propyl p-oxybenzoate and the like)] and the like. The capsule agent may be processed into a conventional capsule, an enteric-coated capsule, a gastric resistant capsule or a controlled release capsule. When an enteric capsule is desired, for example, a mixture coated with the aforementioned enteric coating agent may be filled in a conventional capsule or the capsule itself may be coated with an enteric coating agent, or an enteric polymer may be formed as a capsule base.

When a solid preparation is produced using liposome as a complex, a suspension of the liposome may be concentrated or lyophilized and subjected to production as it is, or the above-mentioned suitable additive and the like are mixed as appropriate to preferably produce a solid preparation. When a liposome is to be lyophilized, addition of a cryoprotectant (e.g., monosaccharide, oligosaccharide, sugar alcohol such as sorbitol, trehalose and the like) is preferable.

BEST MODE FOR EMBODYING THE INVENTION

Figure 1:
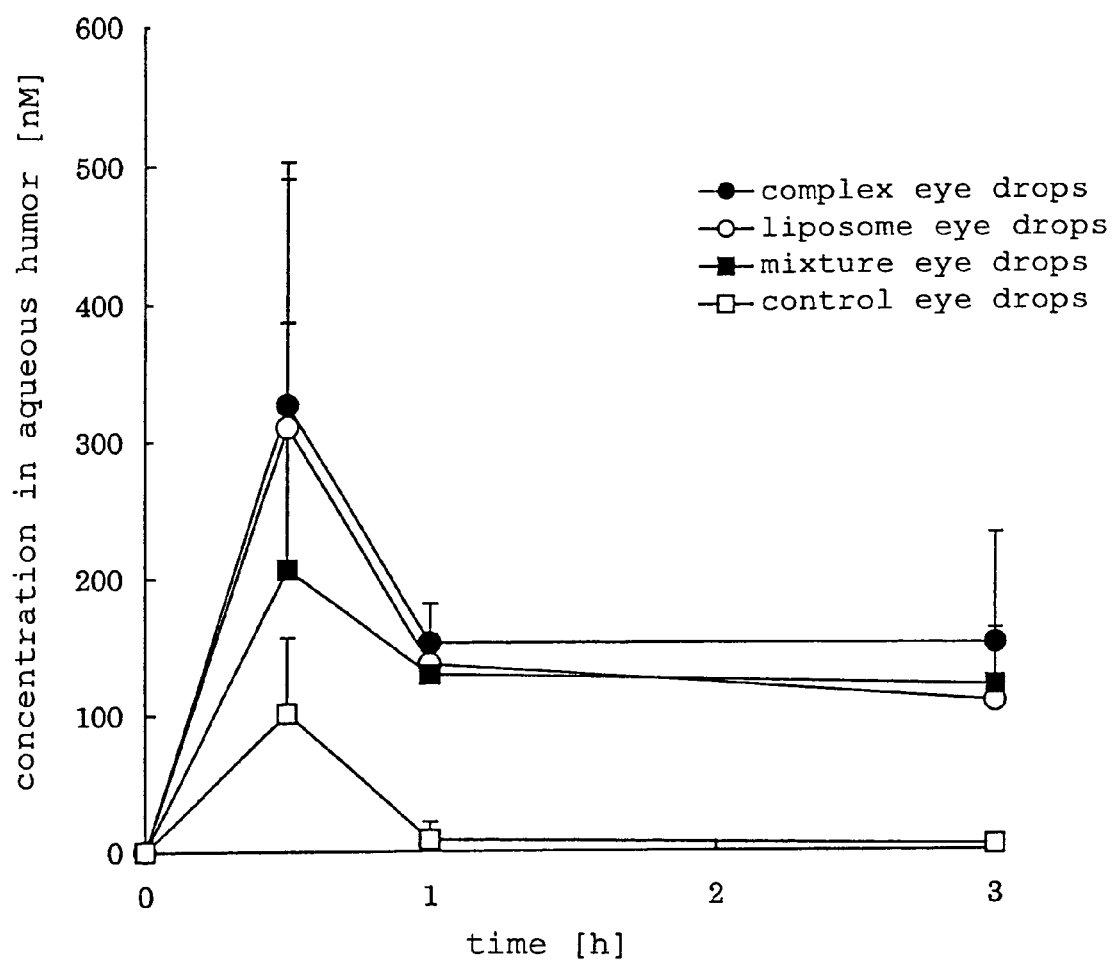
FIG. 1 shows the results of the intraocular penetration test of compound 1 in rabbits in Experimental Example 3.

The present invention is explained in more detail by referring to the following Examples and Experimental Examples, which are not to be construed as limitative. In the following Examples, Experimental Examples and Formulation Examples, compound 1 means N-(4-fluorophenylsulfonyl)-L-valyl-L-leucinal.

EXAMPLE 1

Compound 1-Containing Complex

The compound 1 (0.5 g) and egg yolk lecithin (containing about 70% of phosphatidylcholine and about 30% of phosphatidylethanolamine; 3.5 g) were placed in a 200 mL round-bottom flask and dissolved in chloroform (50 mL). Using a rotary evaporator (RE1-NS, IWAKI), chloroform was removed. The residue was thoroughly dried in a shelf type vacuum dryer to give a complex of compound 1 and egg yolk lecithin.

EXAMPLE 2

Compound 1-Containing Complex

The compound 1 (1.0 g) and egg yolk lecithin (containing about 70% of phosphatidylcholine and about 30% of phosphatidylethanolamine; 10.0 g) were placed in a 300 mL round-bottom flask and dissolved in chloroform (100 mL). Using a rotary evaporator (RE1-NS, IWAKI), chloroform was removed. The residue was thoroughly dried in a shelf type vacuum dryer to give a complex of compound 1 and egg yolk lecithin.

EXAMPLE 3

Compound 1-Containing Complex

The compound 1 (0.5 g) and egg yolk lecithin (containing about 70% of phosphatidylcholine and about 30% of phosphatidylethanolamine; 2.5 g) were placed in a 200 mL round-bottom flask and dissolved in chloroform (50 mL). Using a rotary evaporator (RE1-NS, IWAKI), chloroform was removed. The residue was thoroughly dried in a shelf type vacuum dryer to give a complex of compound 1 and egg yolk lecithin.

EXAMPLE 4

Compound 1-Containing Complex

The compound 1 (0.5 g) and phosphatidylcholine dipalmitoyl (3.5 g) were placed in a 200 mL round-bottom flask and dissolved in chloroform (50 mL). Using a rotary evaporator (RE1-NS, IWAKI), chloroform was removed. The residue was thoroughly dried in a shelf type vacuum dryer to give a complex of compound 1 and phosphatidylcholine dipalmitoyl. The complex obtained in this Example was subjected to thermal analysis and formation of a complex was confirmed.

EXAMPLE 5

Compound 1-Containing Liposome

The compound 1 (0.5 g), egg yolk lecithin (containing about 70% of phosphatidylcholine and about 30% of phosphatidylethanolamine; 3.5 g) and cholesterol (1.5 g) were placed in a 200 mL round-bottom flask and dissolved in chloroform (50 mL). Using a rotary evaporator (RE1-NS, IWAKI), chloroform was removed to form a lipid thin membrane on the wall of the flask. A solution (100 mL, pH 7.0) of sodium dihydrogenphosphate dihydrate (0.1 g) and sodium chloride (0.9 g) in sterile purified water (100 mL) was added to this flask, and the mixture was shaken well in a vortex mixer. This solution was ultrasonicated in a sonicator (MODEL UR-200P, TOMY SEIKO) for 15 min to give a suspension of compound 1-containing liposome. The suspension obtained in this Example was confirmed to contain compound 1 in a proportion of 0.5 w/v %.

EXAMPLE 6

Compound 1-Containing Liposome

The compound 1 (1.0 g), egg yolk lecithin (containing about 70% of phosphatidylcholine and about 30% of phosphatidylethanolamine; 7.0 g) and cholesterol (3.0 g) were placed in a 300 mL round-bottom flask and dissolved in chloroform (100 mL). Using a rotary evaporator (RE1-NS, IWAKI), chloroform was removed to form a lipid thin membrane on the wall of the flask. Sterile purified water was added to this flask to make the total amount 200 mL. The mixture was shaken well in a vortex mixer. This solution was ultrasonicated in a sonicator (MODEL UR-200P, TOMY SEIKO) for 15 min to give a suspension of compound 1-containing liposome. The suspension obtained in this Example was confirmed to contain compound 1 in a proportion of 0.5 w/v %.

EXAMPLE 7

Compound 1-Containing Liposome

The compound 1 (0.5 g) and egg yolk lecithin (containing about 70% of phosphatidylcholine and about 30% of phosphatidylethanolamine; 3.5 g) were placed in a 200 mL round-bottom flask and dissolved in chloroform (50 mL). Using a rotary evaporator (RE1-NS, IWAKI), chloroform was removed to form a lipid thin membrane on the wall of the flask. A 0.1 w/v % aqueous trehalose solution (100 mL) was added to this flask and the mixture was shaken well in a vortex mixer. This solution was ultrasonicated in a sonicator (MODEL UR-200P, TOMY SEIKO) for 10 min. The obtained liposome suspension was freeze-dried using a vacuum freeze dryer (LYPH LOCK6, LABCONCO) to give a freeze dry product of compound 1-containing liposome.

EXAMPLE 8

Compound 1-Containing Mixture

The compound 1 (0.5 g) and egg yolk lecithin (containing about 70% of phosphatidylcholine and about 30% of phosphatidylethanolamine; 3.5 g) were placed in a mortar and triturated to give a mixture of compound 1 and egg yolk lecithin.

EXAMPLE 9

Compound 1-Containing Mixture

The compound 1 (0.5 g) and phosphatidylcholine dipalmitoyl (3.5 g) were placed in a mortar and triturated to give a mixture of compound 1 and phosphatidylcholine dipalmitoyl.

EXPERIMENTAL EXAMPLE 1

Stability Test (Test Substances)
Composition of the present invention: A suspension of the compound 1-containing liposome prepared in Example 5 was used.
Control liquid: A 0.5 w/v % compound 1-containing suspension obtained by adding compound 1 to a vehicle (0.9 w/v % sodium chloride, 0.1 w/v % sodium dihydrogenphosphate, 0.1 w/v % polysorbate 80, 0.005 w/v % benzalkonium chloride; pH 7.0) and ultrasonication thereof using an ultrasonic cleaner (SUS-103, Shimadzu) at 28 kHz for 5 min into fine particles was used.

(Test Method)
The composition of the present invention and the control liquid (each 5 mL) were respectively filled in a colorless glass ampoule and preserved in a desktop incubator (CH-M, NAGANO SCIENCE EQUIPMENT MFG. CO., LTD.) set for 60° C. After preservation for 2 weeks and 4 weeks, samples were taken and the residual amount of compound 1 was measured using high performance liquid chromatography (HPLC).

(Test Results)
The results are shown in Table 1.

TABLE 1

Residual amount of compound 1 in the composition of the present invention and control liquid

| | Percent remaining of compound 1 | |
| --- | --- | --- |
| | Composition of invention | Control liquid |
| Initial | 100.0 | 100.0 |
| 60° C., 2 weeks | 91.2 | 73.2 |
| 60° C., 4 weeks | 76.7 | 64.1 |

The percent remaining of compound 1 in the composition of the present invention and the control liquid after preservation at 60° C. for 4 weeks was 76.7% and 64.1%, respectively, and the composition of the present invention was superior to the control liquid in the stability of compound 1. From these test results, it was found that compound 1 had improved stability when encapsulated in a liposome.

EXP RIMENTAL EXAMPLE 2

Intraocular Penetration Test (Test Substances)
The composition of the present invention (liposome eye drops): A suspension of the compound 1-containing liposome prepared in Example 5 was used.
Control eye drops: A 0.5 w/v % compound 1-containing suspension obtained by adding compound 1 to a vehicle (0.9 w/v % sodium chloride, 0.1 w/v % sodium dihydrogenphosphate, 0.1 w/v % polysorbate 80, 0.005 w/v % benzalkonium chloride; pH 7.0) and ultrasonication thereof using an ultrasonic cleaner (SUS-103, Shimadzu) at 28 kHz for 5 min into fine particles was used.

(Test Method)
The liposome eye drops and control eye drops were respectively instilled into one eye of a rabbit (male, body weight about 2 kg) by 50 μL. After 0.5, 1 and 3 hr of instillation, aqueous humor was taken. The concentration of compound 1 in the aqueous humor was measured using HPLC (NANO-SPACE SI-1, SHISEIDO) by column switching system.

(Test Results)

The results are shown in Table 2.

TABLE 2

Penetration test of liposome eye drops and control eye drops into aqueous humor

| | Concentration (nM)* of compound 1 in aqueous humor | | | |
|---|---|---|---|---|
| | Before instillation | 0.5 hr** | 1 hr** | 3 hr** |
| liposome eye drops | 0 ± 0 | 367.1 ± 184.8 | 6.0 ± 7.2 | 0 ± 0 |
| control eye drops | 0 ± 0 | 101.0 ± 56.1 | 8.6 ± 13.0 | 4.1 ± 6.4 |

*; mean ± standard deviation of six eyes
**; time after instillation

In both the liposome eye drops and control eye drops, the concentration of compound 1 in aqueous humor reached the maximum (Cmax) at 0.5 hr after instillation. The amount of compound 1 in the liposome eye drops that penetrated into the aqueous humor at Cmax was about 3.6 times the amount of that in the control eye drops. From the instant test results, compound 1 was found to show improved penetration into an aqueous humor by formulating into a liposome.

The area under the aqueous humor concentration-time curve (AUC) of compound 1 in the aqueous humor is shown in Table 3 for the liposome eye drops and the control eye drops in 0-3 hr.

TABLE 3

AUC of compound 1 in aqueous humor

| | $AUC_{0\rightarrow 3}$ (nM · h) |
|---|---|
| liposome eye drops | 191.0 |
| control eye drops | 65.3 |

The AUC of the liposome eye drops was about 2.9 times higher than that of the suspension.

From the above results, it was found that the composition of the present invention was a preparation superior in intraocular penetration.

EXPERIMENTAL EXAMPLE 3

Intraocular Penetration Test (Test Substances)

The composition of the present invention:

(1) Complex eye drops: A complex (12.0 g) containing compound 1 prepared in Example 1 was added to a solution (270 mL, pH 7.0) of sodium dihydrogenphosphate (0.3 g) and sodium chloride (2.7 g) dissolved in sterile purified water, and mixed at 1500 rpm for 30 min using homomixer (ROBOMIX, TOKUSHU KIKA KOGYO CO., LTD.). Sterile purified water was added to the mixture to make the total amount 300 mL.

(2) Liposome eye drops: A suspension of the compound 1-containing liposome prepared in Example 5 was used.

(3) Mixture eye drops: Sodium dihydrogenphosphate (0.3 g) and sodium chloride (2.7 g) were added to sterile purified water (270 mL) and dissolved. Compound 1 (1.5 g) and egg yolk lecithin (containing phosphatidylcholine (about 70%) and phosphatidylethanolamine (about 30%), 10.5 g) were added and the mixture was stirred at 1500 rpm for 30 min in a homomixer (ROBOMIX, TOKUSHU KIKA KOGYO CO., LTD.). Sodium hydroxide was added and the mixture was adjusted to pH 7.0, and sterile purified water was added to the mixture to make the total amount 300 mL.

Control eye drops: Polysorbate 80 (0.1 g), sodium dihydrogenphosphate (0.1 g), benzalkonium chloride (0.005 g) and sodium chloride (0.9 g) were added to sterile purified water (80 mL) and dissolved. The compound 1 (0.5 g) was added and the mixture was ultrasonicated using an ultrasonic cleaner (SUS-103, Shimadzu) at 28 kHz for 5 min. Sodium hydroxide was added and the pH was adjusted to 7.0. Sterile purified water was added to the mixture to make the total amount 100 mL to give a 0.5 w/v % compound 1-containing suspension, which was used for the test.

(Test Method)

The complex eye drops, liposome eye drops, mixture eye drops and control eye drops were respectively instilled into one eye of a rabbit (male, body weight about 2 kg) by 50 μL. After 0.5, 1 and 3 hr of instillation, the rabbit was sacrificed with pentobarbital and aqueous humor was taken. The concentration of compound 1 in the aqueous humor was measured using HPLC (NANOSPACE SI-1, SHISEIDO) by column switching system.

(Test Results)

FIG. 1 shows the results of concentration of compound 1 in the aqueous humor after administration of the complex eye drops, liposome eye drops, mixture eye drops and control eye drops. In all samples, the concentration of compound 1 in aqueous humor reached the maximum at 0.5 hr after instillation. The complex eye drops, liposome eye drops and mixture eye drops respectively showed about 3.2 times, about 3.1 times and about 2.0 times higher concentration than that of the control eye drops. From the instant test results, composition of the present invention was found to be a preparation superior in penetration into the tissue.

EXPERIMENTAL EXAMPLE 4

Penetration into Blood Test (Test Substances)

The composition of the present invention (liposome liquid): A suspension of the compound 1-containing liposome prepared in Example 6 was used.

Control liquid: A 1.0 w/v % compound 1-containing suspension obtained by adding compound 1 (1.0 g) to a solution of carboxymethylcellulose (0.1 g) in sterile purified water (100 mL) and homogeneous dispersion was used.

(Test Method)

The liposome liquid and control liquid were respectively administered orally using a catheter to a beagle (body weight about 10 kg) at a dose of 100 mg/kg of compound 1. Blood was taken at 0.5, 1, 2, 4 and 8 hr after the administration. Plasma was separated from the blood sample and the concentration of compound 1 in plasma was measured using HPLC (NANOSPACE SI-1, SHISEIDO) by column switching system and taken as the blood concentration of compound 1.

(Test Results)

Figure 2:
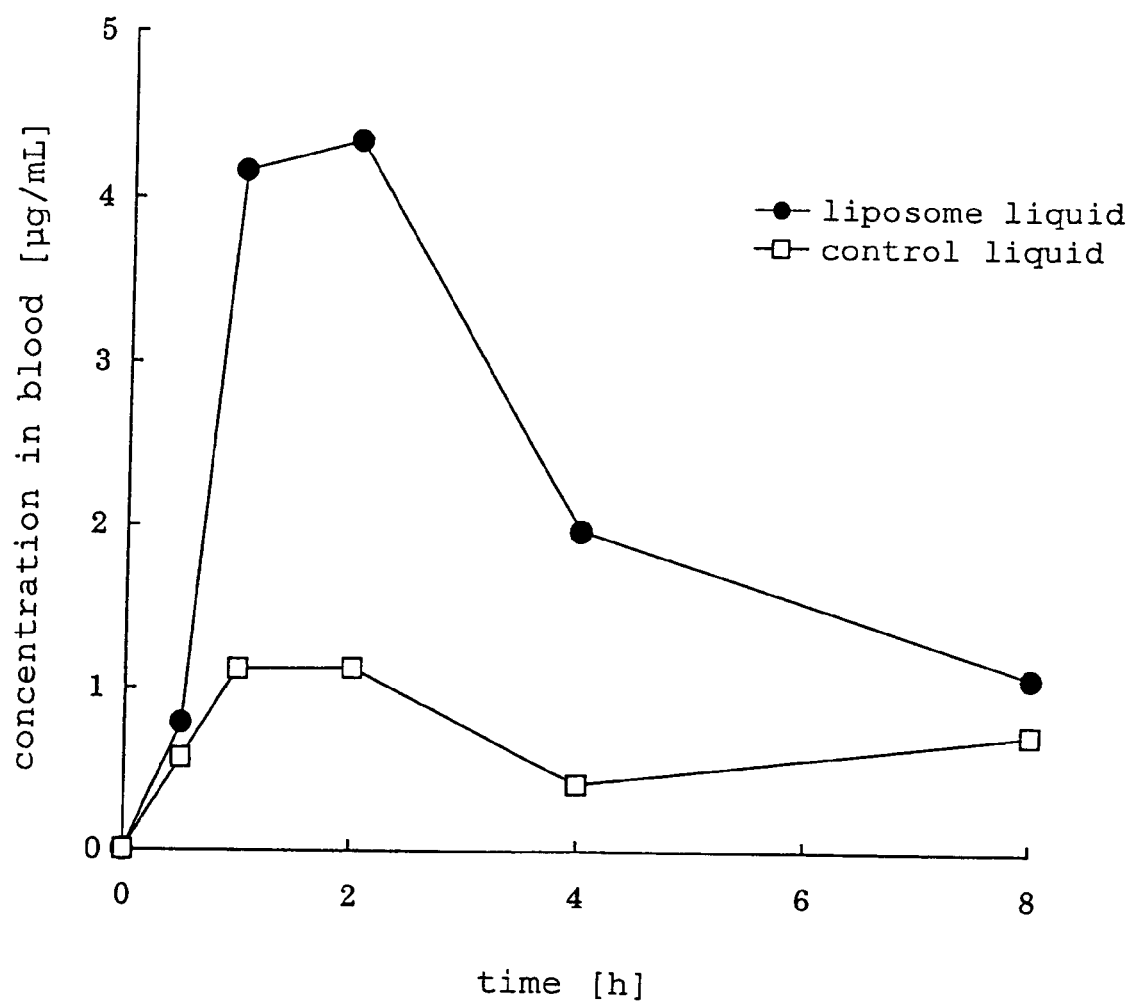
FIG. 2 shows the results of the penetration test of compound 1 into blood in beagles in Experimental Example 4.

FIG. 2 shows the measurement results of the blood concentration of compound 1 after administration of liposome liquid and control liquid. The liposome liquid showed higher blood concentration than the control liquid at any measurement times. While both the liposome liquid and the control liquid reached the maximum blood concentration at 2 hr after the administration, the liposome liquid showed about 3.8 times higher maximum blood concentration than the control liquid. From the test results, it was found that the composition of the present invention was a preparation superior in absorption.

EXPERIMENTAL EXAMPLE 5

Penetration into Blood Test (Test Substances)

The composition of the present invention:

(1) Complex capsule: A complex containing compound 1 prepared in Example 1 was filled in a capsule.

(2) Liposome liquid: A suspension of the compound 1-containing liposome prepared in Example 5 was used.

(3) Mixture capsule: Compound 1 (1.0 g) and egg yolk lecithin (containing phosphatidylcholine (about 70%) and phosphatidylethanolamine (about 30%); 7.0 g) were placed in a mortar, triturated and filled in a capsule.

Control liquid: Compound 1 (0.5 g) was placed in a mortar, 0.5% aqueous carboxymethylcellulose solution (50 mL) was added and triturated to give a compound 1-containing suspension, which was used for the test.

(Test method)

The complex capsule, liposome liquid and mixture capsule were respectively administered orally to a beagle (body weight about 10 kg) at a dose of 50 mg/kg of compound 1, and the control liquid was administered orally to a beagle (body weight about 10 kg) at a dose of 100 mg/kg of compound 1. Blood was taken at 0.5, 1, 2, 4 and 8 hr after the administration. Plasma was separated from the blood sample and the concentration of compound 1 in plasma was measured using HPLC (NANOSPACE SI-1, SHISEIDO) by column switching system and taken as the blood concentration of compound 1.

(Test Results)

Figure 3:
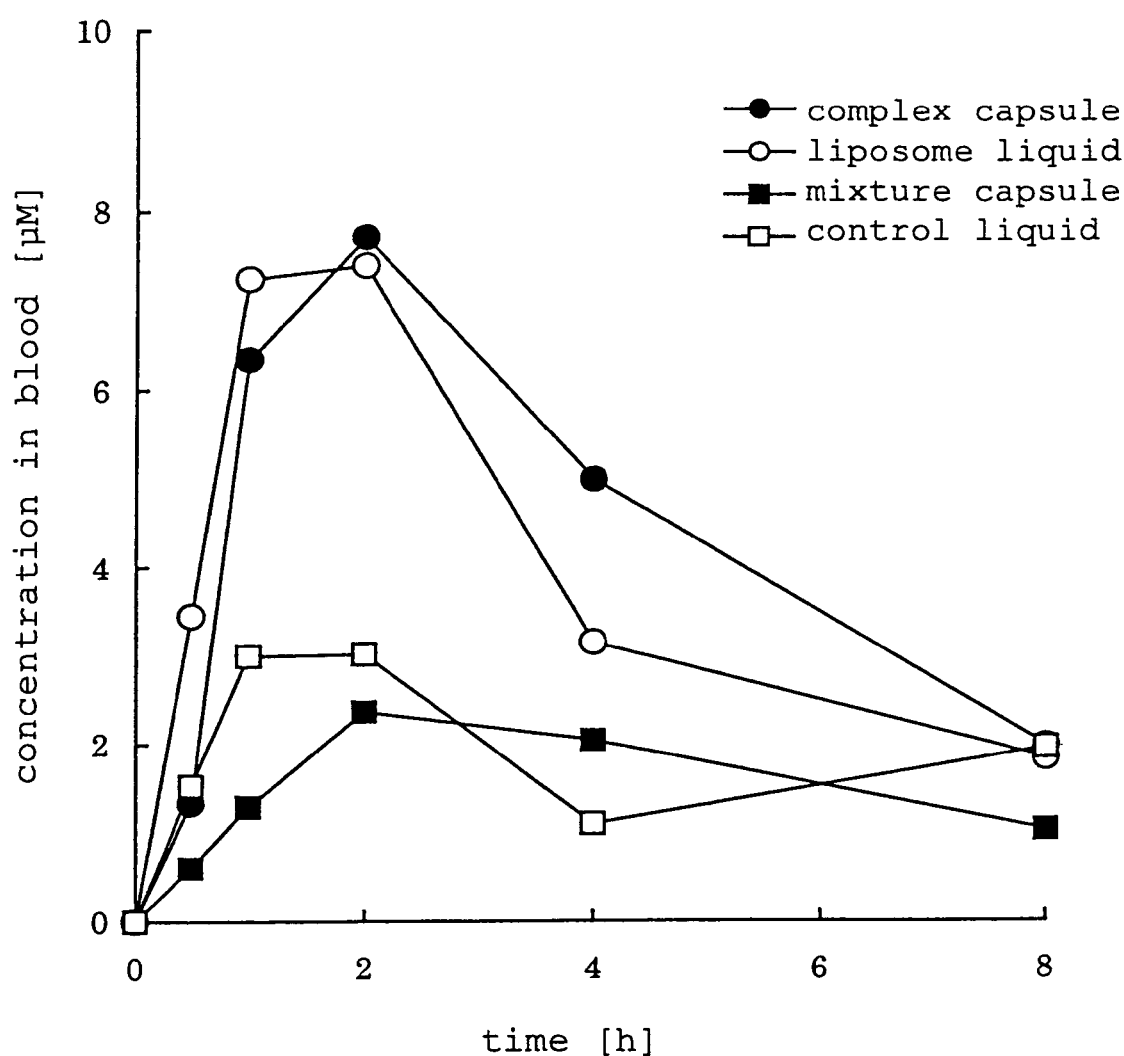
FIG. 3 shows the results of the penetration test of compound 1 into blood in beagles in Experimental Example 5.

FIG. 3 shows the measurement results of the blood concentration of compound 1 after administration of the complex capsule, liposome liquid, mixture capsule and control liquid. In all administration samples, the blood concentration reached the maximum at 2 hr after administration. The maximum blood concentration was almost the same for the complex capsule and liposome liquid, and was about 2.4 times and about 2.6 times, respectively, higher than that of the control liquid containing compound 1 in a 2-fold amount relative to that in the complex capsule and liposome liquid. In the mixture capsule, the amount of penetration into blood was slightly lower than that in the control liquid, despite the fact that the amount of compound 1 was half the amount in the control liquid. From the test results, it was found that the composition of the present invention was a preparation superior in absorption.

| Formulation Example 1: eye drops | |
|---|---|
| Compound 1 | 0.2 g |
| phosphatidylcholine | 1.2 g |
| phosphatidylethanolamine | 1.2 g |
| sodium acetate | 0.1 g |
| sodium chloride | 0.9 g |
| methyl p-oxybenzoate | 0.0026 g |
| propyl p-oxybenzoate | 0.0015 g |
| sterile purified water | total amount (100 mL) |

The compound 1, phosphatidylcholine and phosphatidylethanolamine were placed in a 100 mL round-bottom flask and dissolved in diethyl ether. Diethyl ether was removed using a rotary evaporator (RE1-NS, IWAKI) to form a lipid thin membrane on a flask wall surface. To this flask was added a solution (100 mL, pH 5.0) of sodium acetate, sodium chloride, methyl p-oxybenzoate and propyl p-oxybenzoate in sterile purified water and the mixture was shaken well in a vortex mixer. The mixture was ultrasonicated using a sonicator (MODEL UR-200P, TOMY SEIKO) for 10 min to give a compound 1-containing liposome eye drops.

| Formulation Example 2: injection | |
|---|---|
| Compound 1 | 0.1 g |
| phosphatidylcholine | 0.7 g |
| cholesterol | 0.3 g |
| sodium dihydrogenphosphate | 0.1 g |
| sodium chloride | 0.9 g |
| distilled water for injection | total amount (100 mL) |

The compound 1, phosphatidylcholine and cholesterol are placed in a 100 mL round-bottom flask and dissolved in ethanol. Ethanol is removed using a rotary evaporator (RE1-NS, IWAKI) to form a lipid thin membrane on a flask wall surface. To this flask is added a solution (100 mL, pH 7.0) of sodium dihydrogenphosphate and sodium chloride in distilled water for injection and the mixture is shaken well in a vortex mixer. The mixture is ultrasonicated using a sonicator (MODEL UR-200P, TOMY SEIKO) for 10 min to give a compound 1-containing liposome injection.

| Formulation Example 3: capsule | |
|---|---|
| Compound 1 | 5 g |
| egg yolk lecithin | 50 g |
| lactose | 45 g |

The compound 1 and egg yolk lecithin (containing phosphatidylcholine (about 70%) and phosphatidylethanolamine (about 30%)) are placed in a 100 mL round-bottom flask and dissolved in ethanol. Ethanol is removed using a rotary evaporator (RE1-NS, IWAKI) to form a lipid thin membrane on a flask wall surface. To this flask are added lactose and sterile purified water (100 mL), and the mixture is shaken well in a vortex mixer. The mixture is ultrasonicated using a sonicator (MODEL UR-200P, TOMY SEIKO) for 10 min to give a suspension of compound 1-containing liposome. The obtained suspension is freeze dried, dispensed and filled in 200 capsules.

| Formulation Exampl 4: eye drops | |
|---|---|
| Compound 1 | 0.01 g |
| soybean lecithin | 0.1 g |
| sodium dihydrogenphosphate | 0.1 g |
| sodium chloride | 0.9 g |
| benzalkonium chloride | 0.005 g |
| sodium hydroxide | q.s. |
| sterile purified water | total amount (100 mL) |

Sodium dihydrogenphosphate, benzalkonium chloride and sodium chloride are added to sterile purified water (about 90 mL) and dissolved. Compound 1 and soybean lecithin (containing phosphatidylcholine (about 70%) and phosphatidylethanolamine (about 30%)) are added and the mixture is stirred at 3000 rpm for 30 min in a homomixer (ROBOMIX, TOKUSHU KIKA KOGYO CO., LTD.). Sodium hydroxide is added and the mixture is adjusted to pH 7.0, and sterile purified water was added to the mixture to make the total amount 100 mL.

| Formulation Example 5: injection | |
|---|---|
| Compound 1 | 0.2 g |
| phosphatidylcholine | 0.6 g |
| cholesterol | 0.6 g |
| stearylamine | 0.4 g |
| sodium chloride | 0.9 g |
| sodium dihydrogenphosphate | 0.1 g |
| distilled water for injection | total amount (100 mL) |

The compound 1, phosphatidylcholine, cholesterol and stearylamine are placed in a round-bottom flask, and chloroform is added for dissolution. Chloroform is removed by a rotary evaporator (RE1-NS, IWAKI) and a lipid thin membrane is prepared. Thereto is added a solution (100 mL, pH 7.4) of sodium chloride and sodium dihydrogenphosphate dissolved therein and the mixture is mixed well in a vortex mixer.

INDUSTRIAL APPLICABILITY

The pharmaceutical composition of the present invention shows improved stability by the coexistence of dipeptidyl aldehyde derivative (I) or a pharmaceutically acceptable salt thereof and a lipid, and shows an absorption-promoting action and improved penetration into tissue. Therefore, it is highly useful as a pharmaceutical preparation for the prophylaxis or treatment of ischemic disease, immune disease, Alzheimer's disease, osteoporosis, diseases due to brain tissue impairment (e.g., cerebral vasospasm, cerebral thrombosis, cerebral infarction, cerebral embolism, intracerebral hemorrhage, subarachnoid hemorrhage, hypertensive encephalopathy, transient cerebral ischemic attack, multiinfarct dementia, cerebral arteriosclerosis, Huntington's disease and the like), cataract, glaucoma (e.g., open angle glaucoma, low tension glaucoma, closed angle glaucoma and the like), retinochoroidal disorders (e.g., retinal vascular abnormalities such as occlusion of retinal vessels, retinal periphlebitis, Eales' disease, ischemic ophthalmic syndrome, retinal arteriolar macroaneurysm and the like, retinopathy due to hypertension or renal disease, diabetic retinopathy, retinal pigment epitheliopathy, retinal dystrophy, macular dystrophy, retinochoroidal atrophy, chorioretinopathy, macular degeneration, macular edema, detachment of the retinal pigment epithelium, detachment of the retina, degenerative retinoschisis, retinoblastoma, retinal pigment epithelium tumor, optic disc capirally angioma and the like), eyeball posterior complications due to photocoagulation (e.g., macular edema, detachment of the retina, optic neuritis, visual field abnormalities, disturbance of light sense, color vision deficiency and the like) and the like, or as a pharmaceutical preparation for the prophylaxis or treatment of angiogenesis, detachment of the retina and the like.

While some of the embodiments of the present invention have been described in detail in the above, it will, however, be evident for those of ordinary skill in the art that various modifications and changes may be made to the particular embodiments shown without substantially departing from the novel teaching and advantages of the present invention. Such modifications and changes are encompassed in the spirit and scope of the present invention as set forth in the appended claims.

This application is based on a patent application No. 2000-327677 filed in Japan, the contents of which are hereby incorporated by reference.

What is claimed is:

1. A mixture or a complex comprising N-(4-fluorophenylsufonyl)-L-valyl-L-leucinal or a pharmaceutically acceptable salt thereof and a lipid selected from the group consisting of glycerophospholipid and glycerophospholipid in combination with sterols.

2. The mixture or the complex of claim 1, comprising between about 5 parts by weight and about 14 parts by weight of the lipid, per 1 part by weight of the N-(4-fluorophenylsulfony)-L-valyl-L-leucinal or pharmaceutically acceptable salt thereof.

3. The mixture or the complex of claim 2, wherein the N-(4-fluorophenylsulfonyl)-L-valyl-L-leucinal or pharmaceutically acceptable salt thereof and the lipid form a complex.

4. The complex of claim 3, wherein the complex is a liposome.

5. The complex of claim 4, wherein the liposome comprises between about 7 and about 14 parts by weight of the lipid, per 1 part by weight of the N-(4-fluorophenylsulfonyl)-L-valyl-L-leucinal or pharmaceutically acceptable salt thereof.

6. A pharmaceutical composition, in the form of an oral composition, comprising the mixture or the complex of claim 1 and a pharmaceutically acceptable additive.

7. A pharmaceutical composition, in the form of eye drops, comprising the mixture or the complex of claim 1 and a pharmaceutically acceptable additive.

8. A pharmaceutical composition, in the form of an injection, comprising the mixture or the complex of claim 1 and a pharmaceutically acceptable additive.

9. A method for improving the stability of N-(4-fluorophenylsulfonyl)-L-valyl-L-leucinal or a pharmaceutically acceptable salt thereof, which comprises bringing the N-(4-fluorophenylsufony)-L-valyl-L-leucinal or pharmaceutically acceptable salt thereof into contact with a lipid selected from the group consisting of glycerophospholipid and glycerophospholipid in combination with sterols.

10. A method for promoting the absorption of N-(4-fluorophenylsulfonyl)-L-valyl-L-leucinal or a pharmaceutically acceptable salt thereof,
which comprises bringing the N-(4-fluorophenylsulfonyl)-L-valyl-L-leucinal or pharmaceutically acceptable salt thereof into contact with a lipid selected from the group consisting of glycerophospholipid and glycerophospholipid in combination with sterols.

11. A method for improving penetration into a tissue of N-(4-fluorophenylsulfonyl)-L-valyl-L-leucinal or a pharmaceutically acceptable salt thereof,
which comprises bringing the N-(4-fluorophenylsulfonyl)-L-valyl-L-leucinal or pharmaceutically acceptable salt thereof into contact with a lipid selected from the group consisting of glycerophospholipid and glycerophospholipid in combination with sterols.

* * * * *